US005985555A

United States Patent [19]

Bertling

[11] Patent Number: 5,985,555

[45] Date of Patent: *Nov. 16, 1999

[54] METHOD AND APPARATUS FOR PROCESSING NUCLEIC ACIDS USING A SMALL TEMPERATURE-CHANGING ZONE

[75] Inventor: Wolf Bertling, Erlangen, Germany

[73] Assignee: Boehringer Mannheim GmbH, Mannheim, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/704,682

[22] PCT Filed: Mar. 16, 1995

[86] PCT No.: PCT/EP95/00975

§ 371 Date: Sep. 19, 1996

§ 102(e) Date: Sep. 19, 1996

[87] PCT Pub. No.: WO95/25592

PCT Pub. Date: Sep. 28, 1995

[30] Foreign Application Priority Data

Mar. 19, 1994 [DE] Germany ............................ 44 09 436

[51] Int. Cl.[6] ............................ C12Q 1/68; C12P 19/34; C12M 1/34

[52] U.S. Cl. ............................ 435/6; 435/91.1; 435/91.2; 435/287.2; 422/68.1

[58] Field of Search ............................ 435/6, 91, 287.2, 435/91.2, 316, 91.5, 810, 289, 290, 299.1; 536/24.3, 24.33; 935/6, 77, 78, 87, 88; 165/267, 268; 436/50; 422/68.1

[56] References Cited

U.S. PATENT DOCUMENTS

| | | | |
|---|---|---|---|
| 4,256,945 | 3/1981 | Carter et al. | 219/10.75 |
| 4,965,188 | 10/1990 | Mullis et al. | 435/6 |
| 5,261,545 | 11/1993 | Ota et al. | 215/1 C |
| 5,427,930 | 6/1995 | Birkenmeyer et al. | 435/91.52 |
| 5,434,049 | 7/1995 | Okano et al. | 435/6 |
| 5,498,392 | 3/1996 | Wilding et al. | 422/68.1 |
| 5,514,785 | 5/1996 | Van Ness et al. | 536/22.1 |
| 5,532,126 | 7/1996 | Chu et al. | 435/6 |
| 5,587,128 | 12/1996 | Wilding et al. | 422/50 |

FOREIGN PATENT DOCUMENTS

| | | |
|---|---|---|
| WO93/13220 | 7/1993 | WIPO . |
| WO93/25912 | 12/1993 | WIPO . |

*Primary Examiner*—Kenneth R. Horlick
*Attorney, Agent, or Firm*—Nikaido Marmelstein Murray & Oram, LLP.

[57] ABSTRACT

Method and device for processing nucleic acids in a reaction mixture on a surface that can be temperature-controlled and its immediate vicinity wherein the main space of the reaction mixture remains essentially isothermal. The method has the advantage of a very short processing time.

37 Claims, 5 Drawing Sheets

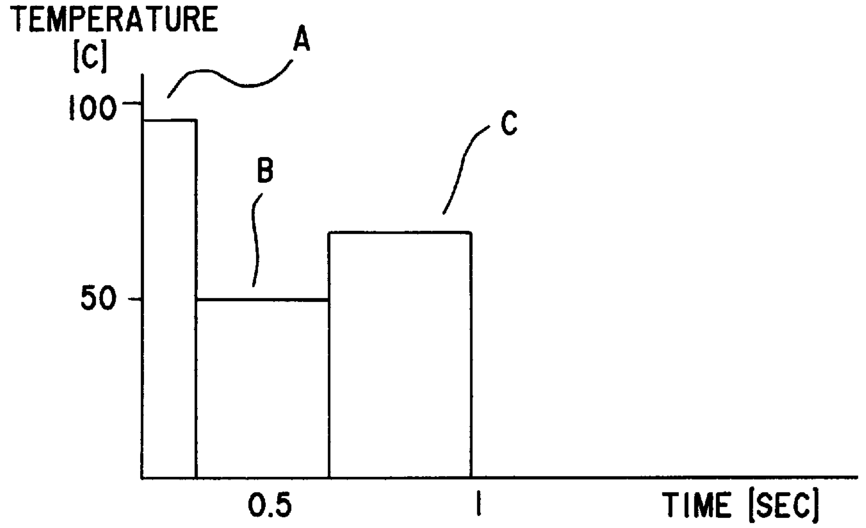
FIG.2
FIG.3A FIG.3B FIG.3C
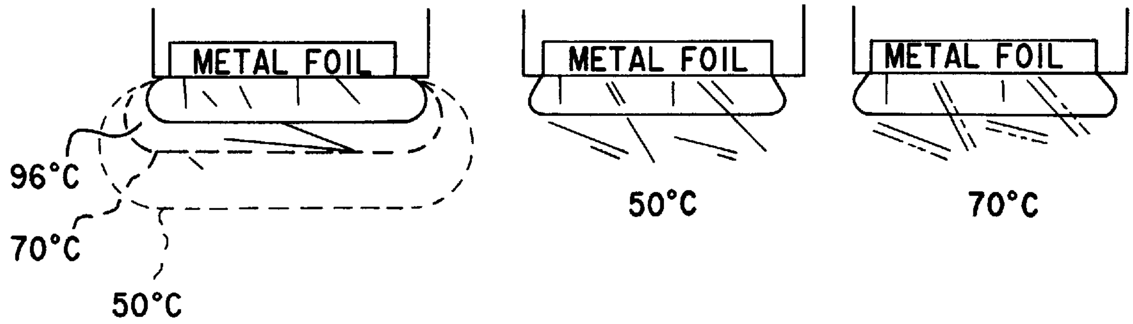

```
                    SEQUENCE LISTING


(1) GENERAL INFORMATION:

   (iii) NUMBER OF SEQUENCES: 3


(2) INFORMATION FOR SEQ ID NO: 1:

     (i) SEQUENCE CHARACTERISTICS:
          (A) LENGTH: 24 nucleotides
          (B) TYPE: nucleic acid
          (C) STRANDEDNESS: single
          (D) TOPOLOGY: linear

    (ii) MOLECULE TYPE: nucleic acid

    (xi) SEQUENCE DESCRIPTION: SEQ ID NO: 1:

     GAAGGGAGGA AGGAGGGAGC GGAC                                       24

(2) INFORMATION FOR SEQ ID NO: 2:

     (i) SEQUENCE CHARACTERISTICS:
          (A) LENGTH: 51 nucleotides
          (B) TYPE: nucleic acid
          (C) STRANDEDNESS: single
          (D) TOPOLOGY: linear

    (ii) MOLECULE TYPE: nucleic acid

    (xi) SEQUENCE DESCRIPTION: SEQ ID NO: 2:

     GAAGGGAGGA AGGAGGGAGC GGACGTCCAC CACCACCCAA CCACCCCACC C         51

(2) INFORMATION FOR SEQ ID NO: 3:

     (i) SEQUENCE CHARACTERISTICS:
          (A) LENGTH: 24 nucleotides
          (B) TYPE: nucleic acid
          (C) STRANDEDNESS: single
          (D) TOPOLOGY: linear

    (ii) MOLECULE TYPE: nucleic acid

    (xi) SEQUENCE DESCRIPTION: SEQ ID NO: 3:

     GGGTGGGGTG GTTGGGTGGT GGTG                                       24
```

METHOD AND APPARATUS FOR PROCESSING NUCLEIC ACIDS USING A SMALL TEMPERATURE-CHANGING ZONE

The invention concerns methods for processing nucleic acids by means of a temperature regulation element as well as devices and instruments for carrying out these methods.

In analytics and especially in medical diagnostics more and more methods are beginning to be established which are based on nucleic acid tests and syntheses. Nucleic acids are for example very well suited as a very specific detection agent for organisms for the diagnosis of diseases. During these detection methods various processing steps such as denaturation, hybridization, syntheses and immobilization of nucleic acids and enzymatic treatment thereof are common. For a long time a problem of such methods was the small amount of nucleic acids in the samples.

A solution for this problem, which has made it possible to detect numerous analytes, was the amplification of nucleic acids. Such a method is described in EP-A-0 200 362 i.e. the polymerase chain reaction (PCR). In this method many copies of the original nucleic acid are produced by repeated extension of primers in a reaction solution. These can for example be detected by hybridization with a labelled nucleic acid probe according to EP-A-0 201 184. The reaction solutions used for this are heated to particular temperatures and cooled again at intervals in order to separate double strands and for the extension reaction. Since the volumes are relatively large, the times required for temperature regulation result in a relatively long period to carry out the entire amplification process.

It has been attempted to remedy this by so-called capillary PCR. In this method the reaction mixture is present in glass capillaries of a small diameter. As a result the time required to carry out an amplification sequence can be reduced to ca. 30 min. A problem with capillary PCR is the delicacy of the glass of the capillary which also has to be heated and the cumbersome sample application.

Recently more and more amplification processes are also being described in which the amplification reactions can be carried out in a closed system i.e. without supplying reagents during the cycles. Thus in a system is described WO 92/07089 in which the amplification mixture is passed as long as necessary through a circulation system in which the reaction mixture is repeatedly heated and cooled. The period in which the mixture is retained in the individual zones of the system can be influenced by selecting the diameter. An amplification process is described in EP 0511712A1 in which the amplification mixture is brought cyclically to quite specific temperatures in order to achieve relatively short cycle times. In this case also the sample handling is made more difficult.

The object of the present invention was among others to improve the existing nucleic acid processing methods and in particular to provide processes in which the amplification can be completed in a particularly short time.

The invention therefore concerns a method for processing and in particular amplifying nucleic acids in a reaction mixture characterized in that the temperature of a surface adjoining the reaction mixture and its immediate surroundings is regulated but the main space of the reaction mixture remains essentially isothermal.

The invention also concerns a device for processing and amplifying nucleic acids with a temperature regulation element as well as an instrument which contains this device.

Nucleic acids within the sense of the invention are all types of nucleic acids, modified or unmodified. Unmodified nucleic acids are for example the naturally occurring nucleic acids. Modified nucleic acids can be formed by substituting groups of the natural nucleic acids by other chemical residues. Examples are nucleic acid phosphonates or phosphothioates and nucleic acids modified on their sugar residues or bases by chemical groups which may also be detectable.

The processing of nucleic acids according to the present invention preferably includes at least one reaction step which proceeds at an increased temperature that is at least different from the ambient temperature. Such reaction steps are for example the thermal denaturation of partially or completely double-stranded nucleic acids. In this process the nucleic acids are heated to temperatures above the relevant melting point in order to produce single strands or to melt secondary structures. A further processing step of nucleic acids is the hybridization of the single-stranded regions of nucleic acids which are complementary to one another to form a nucleic acid double strand (hybrid). This takes place at temperatures below the melting point of the hybrid. Therefore in-order achieve a hybridization it is often necessary to cool the reaction mixture. Especially in amplification or sequencing methods a further processing step is carried out namely the extension of a primer hybridizing to a so-called template nucleic acid with the aid of further mononucleotides or oligonucleotides. In t his case the temperature is preferably adjusted to that at which the enzyme used has its activity optimum or at which competing reactions are reduced. This temperature may also be identical to the hybridization temperature (2-step PCR).

A special case for processing nucleic acids is the amplification of nucleic acids. In this connection practically all amplification methods e.g. target sequence-dependent amplifications (in particular non-isothermal amplifications such as the polymerase chain reaction, ligase chain reaction or similar ones) can be carried out according to the invention. Also during these amplification methods at least one of the aforementioned temperature sensitive processing steps takes place.

A key feature of the present invention is the fact that the change of temperature does not take place in the entire reaction mixture but only in a very small part of the reaction mixture. As a result the heating and cooling of this relatively small zone can occur very rapidly thus considerably accelerating the processing of nucleic acids. Therefore in order to carry out the process according to the invention the reaction mixture is contacted with a surface whose temperature can be regulated. By changing the temperature of the surface the immediate surroundings of this surface are heated, equalized or cooled depending on the processing step and temperature of the reaction mixture. One can differentiate between several cases.

If the temperature of the reaction mixture is higher than the melting temperature of the nucleic acids to be processed, the surface can be cooled in order to achieve a hybridization of the nucleic acids in the adjoining vicinity. If the temperature of the reaction mixture is lower than the melting temperature and the temperature which is required to extend a primer on the nucleic acid, the surface and thus the immediate vicinity can be firstly heated to a temperature at which an extension of the primer can take place. Subsequently the temperature can be increased to above the melting point of the nucleic acids which enables a denaturation and strand separation of the double-stranded nucleic acids which have been formed. This can be followed by cooling to a temperature at which the single strands can hybridize with new primers. This cycle can be repeated several times.

If the temperature for the reaction mixture lies between the optimal temperature for extension and the melting temperature, the temperature at the surface is firstly increased in order to separate double strands. Subsequently the temperature is lowered to a temperature at which the single strands hybridize with primers. Subsequently the temperature is adjusted to an optimum for the extension and if desired the cycle is repeated.

The desired temperature can be maintained over a predetermined period e.g. until the desired reactions have taken place at the surface. For this purpose the temperature of the surface can also be kept constant by known control measures and connected regulation measures (reheating, recooling). The time periods depend, as is usual for the known processes, on the length of the nucleic acids to be processed and their homology as well as on the special hybridization conditions. However, a person skilled in the art can determine the optimum periods by simple experiments. The time periods are between fractions of seconds and a few seconds depending on the processing step.

In the above mentioned cases the main space of the reaction mixture remains essentially isothermal whereas the reaction mixture located in the immediate vicinity of the surface adjusts to the set temperatures of the surface.

In order to regulate the temperature and to set specific temperatures at the surface and its immediate vicinity it is recommended that a surface of a device is selected as the surface that is composed of a heating element and a cooling element. The heating element preferably has a relatively large surface with a comparatively small heat capacity. Metal foils have for example proven to be suitable which can be heated in a suitable manner e.g. by electrical current. Good heat conducting materials such as gold are preferred as materials for the metal foil.

The cooling element should have a relatively high heat capacity. Solid, liquid or gaseous substances come into consideration as the cooling medium. Liquid cooling media such as water are preferred. A good heat conductivity is advantageous.

The arrangement of the heating element and cooling element can be changed according to the temperature of the reaction medium depending on whether it is intended to use the device more for heating or for cooling the surface and its immediate vicinity. However, in general the heating element is located in the immediate vicinity of the surface. The surface of the heating element can also directly adjoin the reaction mixture. However, it is also possible to separate the heating element from the reaction mixture by a thin heat conducting layer.

The cooling element can in principle be positioned at any position which allows a cooling of the surface and the immediate vicinity. However, it has proven to be advantageous to position the cooling element on the opposite side of the reaction mixture to the heating element. If the heating element has a low heat capacity, the fact that the heating element must also be cooled is not an important disadvantage.

In the method according to the invention the heating element is used to heat until the surface and its immediate vicinity have been heated to the desired temperature. In this process a pronounced temperature gradient will form near the surface whereas the remaining part of the reaction mixture remains isothermal. This applies in particular if there is no significant exchange of liquid during the heating process but even if there is an exchange of liquid. The heating process can be completed within fractions of a second and in favourable cases even is milliseconds. The same applies to the cooling. The reaction space which is heated to the desired temperature can be very small, it is preferably less than 0.2 mm particularly preferably less than 0.5 μm deep. The area of the heating element facing the reaction mixture influences the depth of the temperature gradient and its rate of formation. A preferred size of the surface may result from the desired application of the process. Usually the surface is <2 $cm^2$, particularly preferably between 0.2 $cm^2$ and 0.2 $mm^2$. The surface can be smooth or also rough. If the surface is also used at the same time as a carrier for agents for processing nucleic acids it is advantageous to enlarge this surface by surface structures.

The volume of the reaction mixture is of no major practical importance for the invention. It may be a drop with a volume of 20 μl but also a volume of any size. An advantage of the process according to the invention is that the device containing the heating and cooling elements can for example also be inserted into a large vessel containing the reaction mixture in which case the key reactions only take place in a very small boundary region of the surface whereas the remaining reaction space exerts almost no influence on the reaction. On the other hand the samples that are available and amounts of reagent represent a practical limit to the size of the reaction mixture. The reaction volumes will therefore usually lie in a range between 1 ml and 30 μl preferably between 100 μl and 50 μl but it is also for example possible to use very much smaller volumes by applying the reaction mixture onto the temperature-regulating surface.

In order to process nucleic acids these are applied to the temperature-controllable surface or its immediate vicinity. This can be achieved in various ways for example mechanically or by diffusion. The nucleic acids are preferably bound to the surface. This binding can in turn be of various types. A chemical binding is preferred either via adsorption or biospecific interactions. In the case of binding by adsorption, the surface can be covered with a nucleic acid binding reagent. Biospecific interactions can be interactions between nucleic acids and the nucleic acids to be processed (hybridization, complementary part of these nucleic acids) but also interactions between antigens or haptens and antibodies directed against them and receptor-ligand interactions. A preferred type of binding of the nucleic acids to be processed to the surface is via oligonucleotides which are bound covalently to the surface and which are complementary to at least part of the nucleic acid to be processed. However, these oligonucleotides can also be bound to the surface by means of biospecific interactions e.g. biotin-streptavidin.

According to the present invention the binding of the nucleic acids to be processed is preferably reversible. The nucleic acids can be released again after a period depending on the process which is to be carried out by heating the surface and its immediate vicinity. Any desired step can be carried out between the binding and release of the nucleic acid such as chemical reactions and also a separation of the bound nucleic acids from the original reaction mixture and transfer into a new reaction mixture.

In the case of an amplification reaction of nucleic acids the oligonucleotides bound to the surface can be used as primers for elongation or extension using the nucleic acid to be processed as a template. As a result a bound extended primer forms on the nucleic acid to be processed. The nucleic acid used as a template can be detached from the extension product by increasing the temperature and in the next temperature cycle it can act as a template for a new immobilized primer which has not yet been elongated. In this manner it is possible to extend a large amount of primers immobilized on the surface and thus produce copies of parts of the nucleic acid to be processed. The extended (elongated) primers attached to the surface in turn serve to multiply the molecule serving as a template by means of complementary primers. The reagents required to carry out the reactions have either to be kept on hand in the total reaction mixture or they must be added as required. Therefore for an amplification reaction according to the principle of a polymerase reaction (EP-B-0 201 184) the deoxyribonucleotides, a DNA polymerase and a further primer and suitable buffer reagents must be kept in the reaction mixture. In order to prepare other nucleic acid types (e.g. RNA) other reagents e.g. ribonucleotides or RNA-dependent polymerases are provided. This step of the process can take the working temperature of the processing enzyme into particular consideration.

The nucleic acids to be processed can, however, also be bound to the surface by physical methods e.g. by means of a magnet. For this the nucleic acids must, however, be bound to a magnetizable particle. The binding of magnetic particles coated with nucleic acid can be carried out in a reversible manner by locating or inducing a magnet behind the surface. By applying an alternating field it is possible to bind the magnetic particles to the surface or remove them therefrom.

Special embodiments which have some advantageous effects are also conceivable. Thus the efficiency can be increased by increasing the diffusion of the nucleic acids in the reaction mixture by convection. It may also be advantageous to use higher concentrations of the reactants compared to the reaction mixtures usually used. In addition the nucleic acid to be processed can be concentrated at the surface at the start of the reaction by prehybridization.

In the case of an amplification or multiplication of nucleic acids it may be that the number of cycles to be carried out e.g. in a PCR has to be increased in order to produce sufficient amplification product. However, due to the very short cycle time according to the process of the invention this is not a disadvantage.

If the reaction mixture is kept at a relatively low temperature this means that less demands have to be made on the heat stability of the reagents than when the entire reaction mixture is heated several times. Therefore a thermostable polymerase is not absolutely necessary for an amplification reaction and nevertheless it is not necessary to pipette new enzyme into the reaction mixture in each amplification cycle.

Any desired further steps can follow the processing of nucleic acids according to the invention. Thus the nucleic acids can be examined either in a bound state on the surface or in a released state or processed with further reagents.

Thus with the aid of the described amplification process according to the invention it is possible in a simple manner to develop a process for detecting nucleic acids in a sample. For this the surface to which the oligonucleotides acting as a primer are bound is contacted with the sample liquid. Afterwards the temperature of the surface and its immediate vicinity is brought to a temperature which lies above the melting point of the double-stranded nucleic acid contained in the sample. After cooling the surface and its immediate vicinity the nucleic acid to be detected is hybridized with the oligonucleotide. By means of the cycle process as described above numerous copies are produced with the aid of the nucleic acid to be detected which can remain bound to the surface at the end of the amplification reaction. The amount of nucleic acids on the surface can be determined by hybridization with labelled nucleic acid probes and detecting them with the aid of the label. In the case of methods which allow a direct detection of nucleic acid hybrids without a label or of extended single strands (primers) (e.g. according to the principle of surface plasmon resonance) a direct detection is also possible. If labelled primers or mononucleotides are used for the amplification reaction hybridization with a detectable labelled nucleic acid probe is omitted. An approach is also conceivable in which a higher temperature is maintained in the mixture and the surface adopts the lower temperatures necessary for the further steps.

Since the application of the process according to the invention to amplify nucleic acids proceeds practically on a surface, we shall introduce the name 2D amplification for this amplification reaction.

The invention also concerns a device which can be used in the aforementioned processing method. In particular the invention concerns a device for processing nucleic acids by means of a temperature regulation element, this element being suitable for regulating the temperature of the surface and its immediately adjoining vicinity and wherein agents can be bound to this for processing the nucleic acids. These agents can be oligonucleotides and serve for example as primers. This device preferably contains a cooling element as well as a heating element in which the arrangement is preferably as in the processing method described above. This device is preferably very small. It can for example have a thickness of <5 mm and an area of <10 cm$^2$. The elements located therein such as the cooling element or the heating element are simple components. Therefore this device is excellently suitable for single use (disposable) which can reduce the risk of contamination that is inherent to re-usable devices. If the device is to be suitable for multiple use, it is also possible to separate the heating element by a very thin component from the space which contains the reaction mixture and to make this component separable from the device. A new component can then be inserted for a further processing step.

The invention also concerns an instrument for processing nucleic acids which contains a control element for a time-dependent temperature regulation as well as a device according to the invention. The control element of a so-called thermocycler according to EP-A-0 236 069 can be used as the control element; however, a control according to the principle of ink-jet printers is preferred since they have a higher control rate. The control element must be able to heat the heating element at predetermined intervals until the vicinity of the surface has an adequate temperature. It must also be able to provide a cooling of the surface by means of a cooling element at predetermined intervals. For this a cooling liquid can for example be passed through the device. Provided the heat capacity of the heating element is small but the heating efficiency is relatively high, a continuous cooling is also possible. Various forms can be used as the surface in an ohmically temperature controlled version of this instrument which can be thermally heated depending on the voltage and the duration of the current. In a modified version the surface to be temperature controlled is located on a preferably black support, preferably a plastic foil, which is heated by a laser ray, preferably an infrared laser, on the side distal to the surface to be temperature controlled. The surface to be temperature controlled as well as the heat-absorbent and heat-conducting material can in this case be mounted on a support surface preferably glass that is permeable to infrared.

The device according to the invention can have various embodiments. For example it can be designed to be immersed in a vessel. However, it can also be designed such that the liquid containing the nucleic acid to be processed is dripped onto the surface or is dispensed into a vessel formed by the surface. This reaction space can also be closed after filling it with the liquid so that contamination problems can be reduced.

One embodiment of the invention is a process for amplifying nucleic acids. This is as in example 3, for example an amplification reaction denoted polymerase chain reaction with subsequent detection.

A further embodiment of the process according to the invention is a process for concentrating nucleic acids e.g. by hybridization. When primers with an adequate specificity are adsorbed covalently onto the surface, it is possible to preset a hybridization temperature when the reaction solution to be analysed has a known composition (ionic composition, concentration of reagents) such that the nucleic acid to be analysed binds specifically to the primers bound covalently to the surface for hybridization. This process can be used a) to exactly analyse the actual hybridization temperature b) to achieve an exact concentration of the nucleic acid to be analysed in the reaction mixture c) to test for the presence of cross-hybridizing sequences.

This short list is not definitive.

This process can also be used to transfer nucleic acids from one solution into another. Then a hybridization takes place in the first vessel (lower temperature) and a denaturation in the second vessel (higher temperature).

A further embodiment of the present invention is a process for sequencing nucleic acids. One method of applying the invention in relation to sequence analyses is the so-called minisequence analysis. In this method the exact sequence of the nucleic acid nucleotide adjoining the primer can be determined by adding exclusively dideoxynucleotides and no deoxynucleotides for sequencing to the solution which is provided for sequencing. The four possible dideoxynucleotides ddATP, ddCTP, ddGTP and ddTTP are labelled with different fluorescent labels. In each case the incorporation of the next respective nucleotide thus leads to a termination of the sequence reaction and, after purification of the extended primer located at the surface, the sequence of the nucleotide located on the primer can be determined by analysis of the specific fluorescence.

A special case for the possible application of the present invention is a process for sequencing nucleic acids which have previously been amplified in a PCR reaction. After the amplification the amplified product is present covalently bound via the primer to the reactive surface in double-stranded form. Denaturation of this amplificate by a brief passage through a high temperature phase will make it single-stranded, will allow it to be purified by transfer to a washing solution and can afterwards be used again for a subsequent sequencing by transfer this time into a sequencing reaction. This sequencing is particularly efficient since now only single-stranded template material is present to which a sequencing pair binds particularly efficiently. As a result of the sequencing reaction a double-stranded molecule is subsequently again present whose labelled (sequenced) half is now available for analysis by gel chromatography. By using different labels (with dideoxynucleotides labelled with different fluorescent markers) all four reactions necessary for a sequence analysis can be carried out simultaneously; with the conventional method this analysis has to be repeated four times.

BRIEF DESCRIPTION OF THE DRAWINGS

The present invention is elucidated in more detail by the following figures.

An example of a temperature curve for an amplification reaction of the PCR type is shown in FIG. 2. In a first phase (A) the nucleic acids are denatured at a temperature of slightly below 100° C. In a phase (B) the nucleic acids to be amplified are hybridized with the immobilized oligonucleotides on the solid phase at about 50° C. In a third phase (C) the primers are extended at ca. 70° C. using the nucleic acid as a template.

FIGS. 3A–3C shows the reactions occurring in the immediate vicinity of the surface (phases A to C). Three isotherms are shown as a schematic time course for phase (A) and only one isotherm is shown for phase (B) and (C) in each case. The nucleic acids are denatured in phase (A) and diffuse for a certain time as single strands, in phase (B) templates and primers hybridize and in phase (C) primers are extended along the templates.

Figure 1:
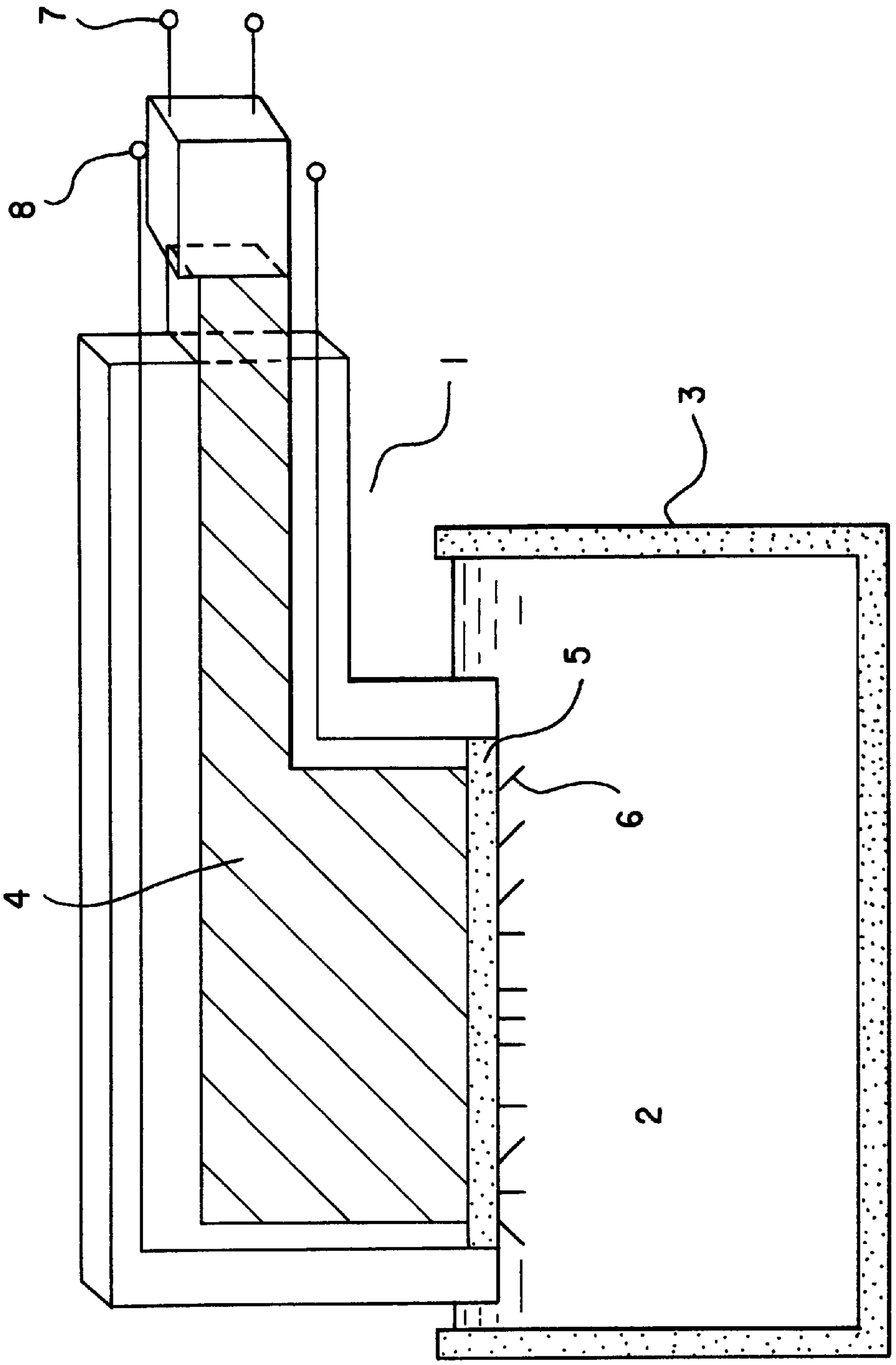
FIG. 1 shows the construction diagram of a device according to the invention (1) which dips into a reaction vessel (3) filled with the reaction mixture (2). The device contains a cooling element (4) and a heating element (5) heated by means of a current. Oligonucleotides (6) are covalently bound to the surface of the heating element. The cooling element as well as the heating element can be regulated via connections (7; 8) to control units.
Figure 4:
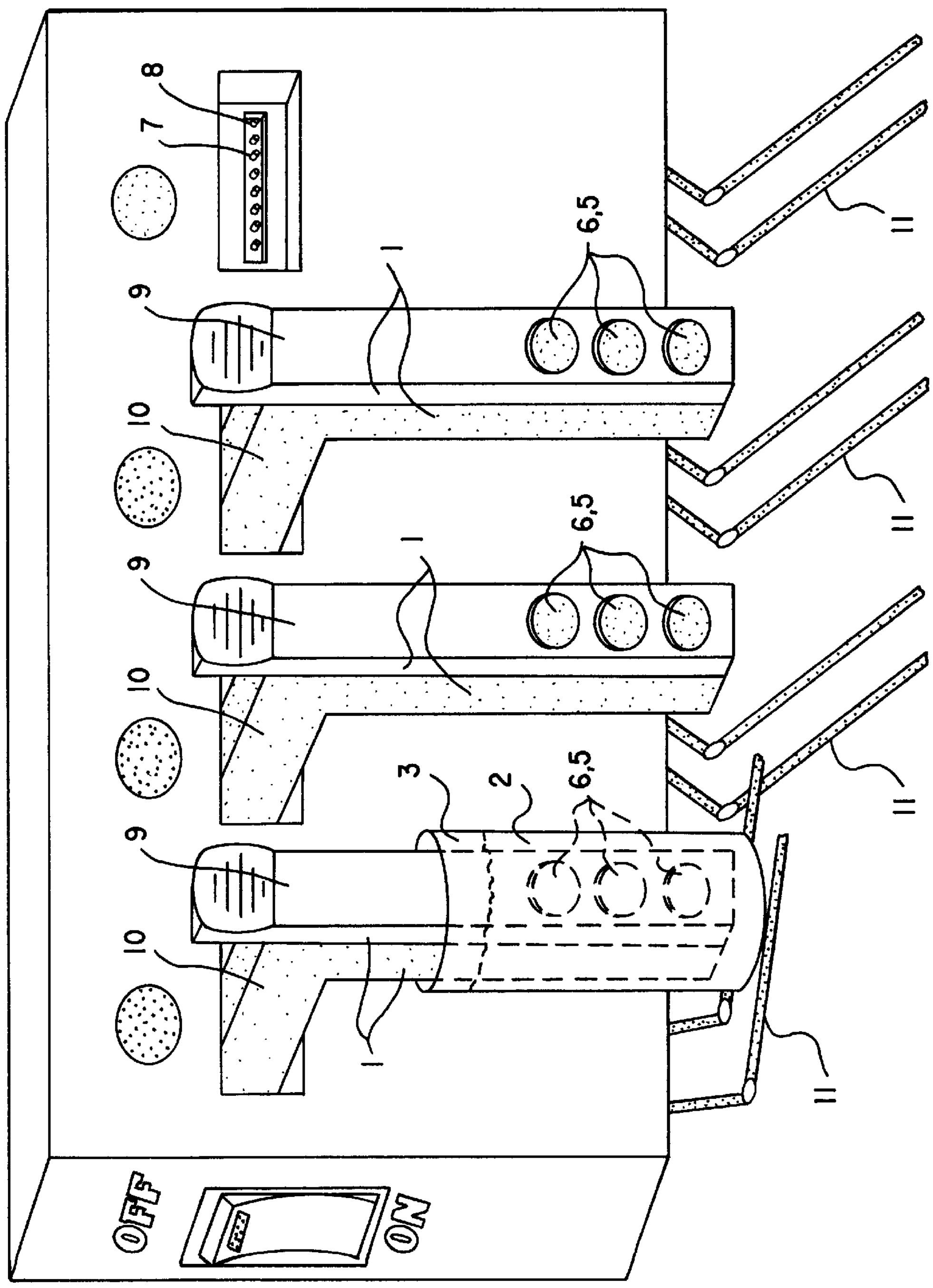

FIG. 4 shows a possible prototype of a surface temperature control suitable for an application according to the invention.

The heating unit which contains the replaceable heated gold surfaces as well as the physical requirements for cooling or heating (connection for cooling agent, electrical connection) is attached via plug connections (7; 8) to the actual measuring unit (1) to which holders for reaction vessels (11) are also attached in which the template molecules, buffer components and primers in solution and the polymerase required for carrying out the reaction are present.

The measuring sensors (9) in this case in the form of a test strip contain as an example gold surfaces (5) in FIG. 4 which do not have to be coated with the same primers (6).

Figure 5A:
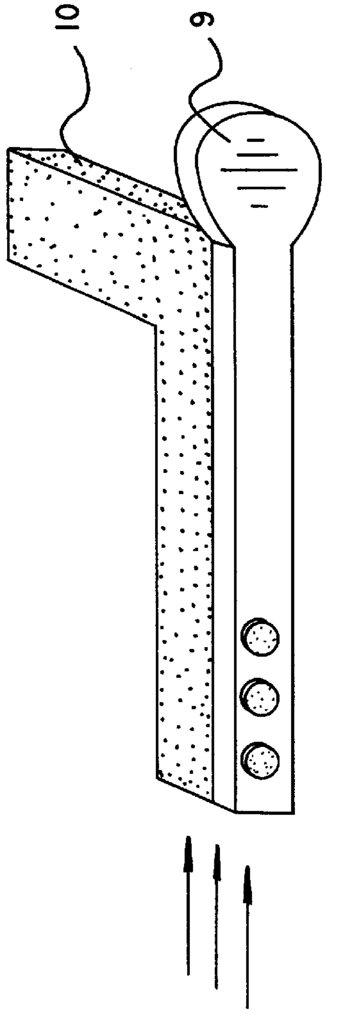
Figure 5B:
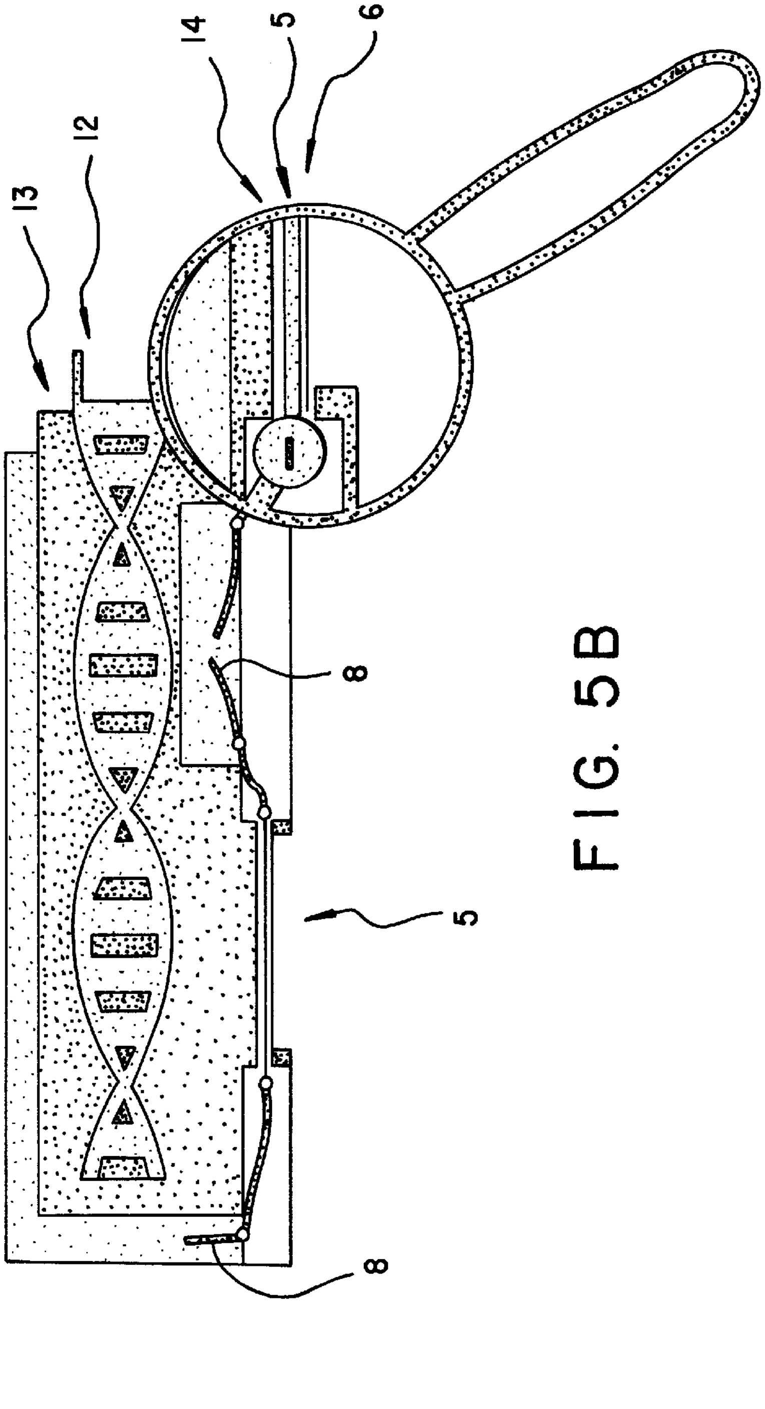

FIG. 5 shows enlargements of the measuring units with replaceable test strips from FIG. 4 in which case the measuring unit (1, composed of 9 and 10) is composed of an electronic connection and cooling system (upper, grey part of the figure) and the test strip (=measuring casing). The lower part of the figure shows a cross-section through this measuring unit which shows the cooling circulation (4) used for the cooling with a stirring mechanism (12) and cooling liquid (13) as well as the reaction surfaces (5, 6) with an electronic connection. The right hand part of the lower figure shows a further enlargement of the cathode connection of the gold membrane (5) with a supporting and separating filter (14) as well as an adhesion layer for the oligonucleotides (6).

Figure 6A:
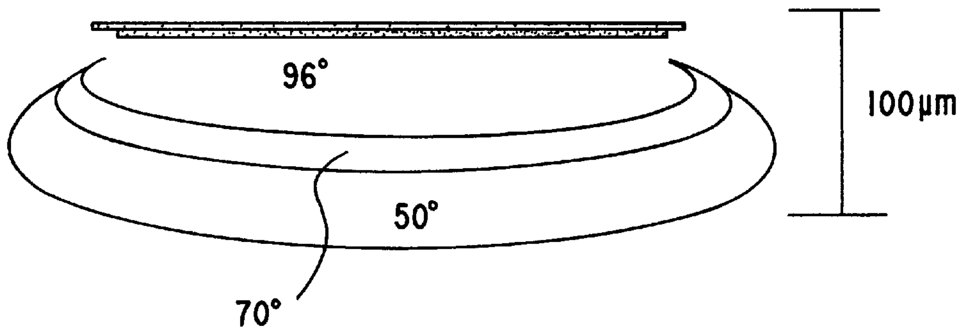
Figure 6B:
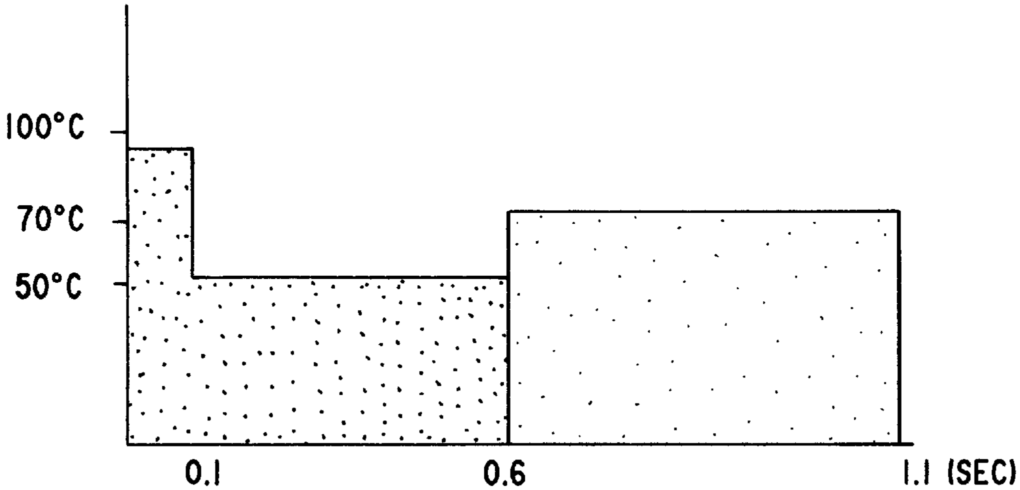

FIG. 6 is composed of a diagram of the temperature gradients formed in the immediate vicinity of the adhesion layer containing oligonucleotides and the temperature profile which is to be expected, in this case as exemplified by a three-step PCR in which temperatures of 96° C. for 0.1 seconds, 54° C. for 0.5 seconds and 72° C. again for 0.5 seconds are shown.

The following examples are intended to further elucidate the invention in more detail:

EXAMPLE 1

Manufacture of a Surface that can be Cyclically Temperature-Controlled (Variant a)

An exemplary gold surface that can be cyclically temperature-controlled can be obtained by milling out two parallel oblong holes of ca. 1 mm width and 3 mm length at a distance of 3 mm to one another in a thin printed-circuit board. On the side which is facing the solution and which is therefore called the proximal side these oblong holes are connected to one another by vapour-deposited gold. On the distal side one of these oblong holes is connected to the anode via the circuit-board conductors the other is likewise attached to the cathode via the circuit-board conductors.

The gold layer on the proximal side is applied by applying a mask of the desired size, in this case 3×3 mm flush, over the two longitudinal surfaces. The inner sides of the longitudinal surface are galvanically coated with copper flush up to the surface. In the following vapourization process which is carried out conventionally the two electrically conductive longitudinal holes are now coated with only a few $\mu$m thick gold layer. The coating process is described in the following:

The gold surface is manufactured by vapour-depositing on "Lexan" polycarbonate foils (manufacturer: General Electric, thickness 0.75 mm) with dimensions of 8×8 cm over a metal mask (d=0.5 mm, aluminium) in a Leybold high-vacuum coating apparatus (Univex 450). The surfaces lie at regular distances which enables the vapour-coated plate to be separated into several units. The thickness of the gold layer is 300 nm. In a further step the multi-gold spot plate is coated with "dilute" biotinthiol binding layers to form a hydrophobic SAM layer. The biotinthiol compound (HS-C12-DADOO-biotin; N,N'-(12-mercaptododecylyl-biotinylyl)-2,2'-diaminoethylglycol diether; 2.94 mg; $5\times 1^{0-5}$ m) and the diluent (12-mercaptoundecanol, 9.2 mg, $4.5\times 10^{-4}$ m) were dissolved in 100 ml ethanol p.a. The freshly coated polycarbonate foils were immersed in this solution. After 4 hours the plates were taken out, washed twice with ethanol p.a. and immediately coated with streptavidin. For this purpose the gold spots and the SAM-coated foils were immersed for 1 hour in a streptavidin solution (streptavidin concentration: 0.5 mg/ml in 0.05 M potassium phosphate buffer pH 7.2). The surfaces treated in this way were subsequently treated with a washing solution (50 mM potassium phosphate buffer pH 7.2, 2% sucrose, 0.9% NaCl, 0.3% bovine serum albumin fraction II) and afterwards dried for 20 h (25° C. and 40% humidity).

The very small thickness of the gold layer results in a very small conducting gold cross-section (3 mm×3 $\mu$m over a length of 3 mm). This gold layer therefore represents a relatively high resistance compared to the circuit-board conductors.

The conductors are now connected to a current supply which enables the computer-aided control of the ohmically induced temperature of the gold surface.

Manufacture of a Surface that can be Cyclically Temperature-Controlled (Variant B)

In one variant of the manufacture of the surface that can be cyclically temperature-controlled a gold layer is vapour-deposited on the covering layer which isolates the measuring meander made of platinum, a commercially available temperature sensor made of platinum (PT 100). If this measuring sensor is now connected to a regulator-controlled voltage source then this sensor can also be used as a heat source for the vapour-coated gold layer. For this it is necessary to pass the current and voltage of the platinum sensor via an analogue divider onto a regulator. The regulated parameter of the regulator is the resistance of the heated platinum element which enables an exact temperature control when normalization of the gold surface temperature with the temperature of the platinum meander has taken place.

EXAMPLE 2

An Example of a Device to Measure the Surface Temperature of a Gold Foil (Variant a)

A gold foil according to example 1, variant a is covered with a mask which allows a ca. 1 mm wide gold thread to be vapour-deposited on the gold foil which protrudes beyond this gold surface and can be connected to a measuring point. A further mask which allows a second thread to be vapour-deposited e.g. of nickel, bismuth or another alloy suitable for temperature measurement, is also prepared. The metal thread lies on the same side of the gold surface as the gold thread (200 nm thick) but its path separates when leaving the gold surface to be temperature-controlled and it leads to a second measuring point as a separate metal thread (300 nm thick). This arrangement of the measuring probes made of gold and a further metal or alloy suitable for temperature measurement enables the thermovoltage (2.2 mV/100°0 Kalvin) to be measured in the area of the gold foil where the two threads of the measuring probe overlap. The temperature at the cold junction is measured with a thermoprecision PT 1000 element (accuracy >1%) and standardized to 10 V (0 V corresponds to 0°, 10 V corresponds to 100°), only amplified and also standardized to 10 V. The sum of the two temperatures is formed in a summation amplifier and used to electronically regulate the respective surface temperature.

EXAMPLE 2b

An Example of a Device for Measuring the Surface Temperature of the Gold Surface From Example 1, Variant b In order to exactly determine the surface temperature of the gold layer it is possible to press together the surfaces of two PT 100 measuring sensors vapour-coated with gold as described in example 1 variant b in such a way that half of the gold-coated area of the heating sensor covers half the area of the measuring sensor and the remaining area in each case is located in the surrounding medium. If only one sensor is now used for measuring and the other one for heating this then allows the temperature of the gold surfaces to be calculated exactly. The temperature at the surface of the sensors exactly corresponds to the mean temperature of the heated and unheated sensor which can both be exactly defined by measuring their resistance. In this way using a temperature sensor used for measurement it is possible to calibrate a whole series of temperature-controllable surfaces and prepare them for carrying out PCR reactions. The temperature gradient between the heated and unheated surface of two surfaces arranged in this manner is ca. 3° C.

EXAMPLE 3

Procedure for a Two-Step PCR Using a Primer that is Immobilized to a Surface

An example of carrying out a polymerase chain reaction uses a biotin-labelled primer that is immobilized on a surface (5'-GAAGGGAGGAAGGAGGGAGCGGAC-3'SEQ ID NO: 1). The 5' end of this primer is coupled via its biotin group to a superficial streptavidin or gold-streptavidin surface. The molar amount of streptavidin or biotin/square millimeter is about 0.2 pmol/mm$^2$. Nanogram amounts or less of the following double-stranded or single-stranded template molecule (only one strand is cited 5'-GAAGGGAGG AAGGAG GGAGCGGACGTCCACCA CCACCCAACCACCCCACCC-3'SEQ ID NO: 2) and an opposite primer at a concentration of between 0.5 $\mu$M and 2

$\mu$M are present in solution. The reaction takes place in commercial PCR buffer (Boehringer Mannheim, instruction enclosure for the enzyme, 8th edition, order no. 1146165) at 1.5 mM $Mg^{2+}$. A commercial Taq-DNA polymerase (Boehringer Mannheim, order no. 1146165) at a concentration of 20 nM is used as the polymerase. The opposite primer (5'-GGGTGGGGTGGTTGGGTGGTGGTG-3'SEQ ID NO: 3) present in solution was labelled with digoxigenin at its 5' end (Patent EP 0324474).

The PCR reaction was carried out at a constant solution temperature of 68° and on a primer-coated surface cyclically varying between 96 and 68°. The cycle duration of the higher temperature in our example varied between 0.1 seconds, 10 seconds and 1 minute, the lower temperature between 0.5 seconds, 20 seconds and 1 minute.

After completing the cyclic heating the solution was cooled to room temperature in the process of which the complementary elongated biotin-labelled and elongated digoxigenin-labelled primer hybridize to one another and double-stranded DNA fragments are formed. After washing with PCR buffer solution the surfaces were reacted with anti-Dig-POD, incubated for 30 minutes, washed again and admixed with ABTS (colour protocol according to the instruction enclosure item 3 of the Boehringer Mannheim Reverse-Transcriptase-Assay, non-radioactive, order no. 1468120). The coloured product that forms was determined quantitatively in an ELISA photometer at a wavelength of 405/490 nanometers. The absorbance values obtained prove an amplification of a region of the template measured as the extended opposite primer that hybridizes to the primer coupled to the solid phase. In typical experiments we obtained absorbance values of 0.4 when measuring in an ELISA reader and after correcting the digoxigenin-free blank value. The values in control experiments without template were 0.04 after correcting the blank value and in controls without polymerase or without temperature increase but using the complete reaction mixture the values were 0.07. Even when heating the surface for several minutes (5 minutes) the ambient temperature in the constantly temperature-controlled solution only increased by 7° C. even when a significantly (100-fold) larger surface (3 $cm^2$) was heated.

EXAMPLE 4

Manufacture of a Device According to the Invention

An example of a device according to this invention is composed of three structural units. These three structural units are 1. the heatable temperature-controllable surface which penetrates into the liquid reaction medium
2. the components that are necessary for heating and cooling that are connected to
3. the electronic control.

The surface of the element described in this example is composed of a thin gold foil with a thickness of less than half a millimeter which is firmly bound to a streptavidin layer. The biotin-labelled oligonucleotides required for the further processing steps can likewise be applied to this dextran layer by means of affinity coupling. These oligonucleotides are then coupled covalently via their 5' phosphate end to the surface and thus have a reactive 3' end which is accessible to enzymes.

This gold foil which can be structurally stabilized by a supporting plastic net and which has a reactive surface of about 5×5 mm serves at the same time as the heating element since it is connected to an electric power source which leads to a spontaneous heating of this gold foil when current flows. The cooling element is located distally to the reaction mixture, behind the gold foil. In this case the cooling element is composed of a channel recessed in plastic which adjoins the gold foil with an area of 7 mm in width. The channel is 2 mm in depth and runs along the complete length of that part of the instrument denoted measuring sensor which in this case comprises the heating element and cooling element as well as the reactive surface. This channel runs from one end of the measuring sensor to the other end of the measuring sensor at which the reactive surface is applied and back again by inclusion of a cross-piece that separates the two channels. In this component denoted coolant loop a suitable cooling liquid e.g. water is circulated. The entire unit is cast in hard plastic and can be recycled i.e. the gold foil as well as the plastic are reusable.

The control of the heating the reactive surface as well as of the circulation rate and precooling temperature of the coolant is achieved by means of a third electronic component which is attached outside the measuring sensor. This third unit also comprises the storage vessel as well as the connectors for the cooling liquid. In addition there is a micropump in this third unit which is responsible for circulating the cooling liquid. The measuring sensor is made ready-to-use by flanging the coolant pipes onto the measuring unit and connecting the power source to the reactive surface. The individual temperature ranges as well as the duration of action influence on this surface can be preselected via an input unit that is attached to the surface of the control unit and has a digital display.

EXAMPLE 5

Procedure for an Amplification Reaction with the Aid of the Device According to the Invention This example of an application of the device according to the invention is an amplification reaction of a predetermined nucleic acid sequence denoted polymerase chain reaction. Two primers each with a length of 16 bases that code at a distance of 4 nucleotides to one another have been selected for this nucleic acid sequence. The sequence of one of the primers is identical to and that of the other one is complementary to the sequence to be analysed. The primer denoted identical in this case is coupled to the reactive surface via a biotin label present at the 5' end. The other complementary primer as well as all further reagents that are usually used in a so-called PCR reaction are added to the reaction mixture. The reaction is started by setting the respective reaction temperatures that are to predominate in the immediate vicinity of the reactive surface and by immersing the reactive surface or the measuring sensor (see example 4) into the reaction mixture. The temperature changes in the reactive surface are programmed such that 50 heating and cooling cycles can be carried out within ca. 1 minute. The surface is freed of all non-covalently bound reaction partners by subsequent immersion of the measuring sensor into a solution of distilled water and briefly heating it. For analysis the surface purified in this way that now only contains primer molecules and extended primer molecules is introduced together with the measuring sensor into an apparatus which enables a direct determination of the amount of extended product based on plasmon resonance.

LIST OF REFERENCE SYMBOLS

1. device, measuring unit according to the invention
2. reaction mixture
3. reaction vessel

4. cooling element
5. heating element/surface
6. oligonucleotides
7. connections for the cooling element
8. connections for the heating element
9. replaceable measuring sensor
10. electronic connection and cooling system
11. holder for reaction vessel
12. stirrer
13. coolant
14. supporting and separating filter (separating the coolant)

adjoins the temperature-changing zone, the temperature-changing zone is relatively small as compared to the entire reaction mixture and comprises an area less than 0.2 mm in length from the surface, and reagents capable of binding to the nucleic acids to be processed are bound to the surface.

2. The method of claim 1, wherein the reagents are oligonucleotides.

3. A method for detecting nucleic acids in a reaction mixture, comprising

I claim:

1. A method for rapid processing of nucleic acids in a reaction mixture, the method comprising temperature-regulating the reaction mixture by changing a temperature of a temperature-changing element to effect a temperature change in a temperature-changing zone which adjoins the temperature-changing element, while maintaining the remaining portion of the reaction mixture at essentially isothermal conditions throughout the temperature-regulating step, wherein the temperature-changing element has a surface which providing a reaction mixture containing nucleic acids to be detected and reactants for processing the nucleic acids in a processing procedure;

temperature-regulating the reaction mixture by changing temperatures of a temperature-changing element to effect temperature changes in a temperature-changing zone which adjoins the temperature-changing element, while maintaining the remaining portion of the reaction mixture at essentially isothermal conditions throughout the temperature-regulating step, to amplify any nucleic acids in the temperature-changing zone, wherein the temperature-changing element has a surface which adjoins the temperature-changing zone, the temperature-changing zone is relatively small as compared to the entire reaction mixture and comprises an area less than 0.2 mm in length from the surface, and reagents capable of binding to the nucleic acids to be processed are bound to the surface; and detecting the amplified nucleic acids.

4. The method of claim 1, wherein at least one reaction step involved in the processing of the nucleic acids proceeds at an increased temperature in the temperature-changing zone.

5. The method of claim 1, wherein the temperature change in the temperature-changing zone is at least partially accomplished by convection or by stirring the reaction mixture.

6. The method of claim 1, wherein the reaction mixture further comprises further reagents capable of binding to the nucleic acids to be processed.

7. The method of claim 1, in which at least one processing step requires a temperature that differs from the temperature of the reaction mixture.

8. The method of claim 7, wherein a temperature-changing step serves for thermal denaturation.

9. The method of claim 7, wherein a temperature-changing step serves to hybridize nucleic acids.

10. The method of claim 7, wherein a temperature-changing step serves to extend a template molecule.

11. The method of claim 7, wherein various processing steps serve to target sequence-dependently amplify a template molecule.

12. The method of claim 11, wherein a non temperature-resistant DNA polymerase is used for the amplification.

13. The method of claim 11, wherein a temperature-resistant DNA polymerase is used for the amplification.

14. The method of claim 11, wherein RNA-dependent RNA polymerase is used for the amplification.

15. The method of claim 11, wherein RNA-dependent DNA polymerase is used for the amplification.

16. The method of claim 11, wherein DNA ligase is used for the amplification.

17. The method of claim 1, wherein the volume of the reaction mixture is between 20 μl and 1 ml.

18. A system for processing nucleic acids in a reaction mixture, comprising a reaction mixture containing nucleic acids to be detected and reactants for processing the nucleic acids in a processing procedure, and a temperature-changing element which effects temperature changes in a temperature-changing zone of the reaction mixture while maintaining the remaining portion of the reaction mixture at essentially isothermal conditions, wherein the temperature-changing element has a surface which adjoins the temperature-changing zone, the temperature-changing zone is relatively small as compared to the entire reaction mixture and comprises an area less than 0.2 mm in length from the surface, and binding means for binding agents for processing the nucleic acids are bound to the surface.

19. The system of claim 18, wherein the binding means is a chemical or physical binding reagent.

20. The system of claim 18, wherein the binding means is a nucleic acid binding reagent and the agents for processing the nucleic acids are nucleic acids that are complementary to at least a part of the nucleic acids to be processed.

21. The system of claim 18, wherein the temperature-changing element is time-coordinated to effect time-coordinated temperature changes in the temperature-changing zone.

22. The system of claim 18, wherein the binding of the agents is achieved by chemical or biospecific binding.

23. The system of claim 18, wherein the binding means is magnetic particles.

24. The system of claim 23, further comprising a magnet, located behind the surface, which induces a magnetic field to attract the magnetic particles.

25. The system of claim 18, wherein the temperature-changing element is a single-use device.

26. The system of claim 18, wherein only the surface of the temperature-changing element is single-use, and the remainder of the temperature-changing element can be used several times.

27. The system of claim 18, wherein the surface protrudes into the reaction mixture.

28. The system of claim 27, wherein the surface can be cooled and/or heated.

29. The system of claim 18, wherein the temperature of the surface is regulated by a control unit.

30. The system of claim 18, wherein the temperature-changing element comprises a heating element with a small heat capacity and a cooling element with a high heat capacity.

31. The system of claim 30, wherein the heating element is heated ohmically.

32. The system of claim 30, wherein the heating element is heated by rays.

33. The system of claim 32, wherein the rays are infrared rays.

34. The system of claim 32, wherein the rays are laser-generated rays.

35. The system of claim 18, wherein the surface is composed of a foil made of a heat-conducting material.

36. The system of claim 35, wherein the heat-conducting material is metal.

37. The system of claim 36, wherein the heat-conducting material is gold.

* * * * *